United States Patent

Wohlers

[11] Patent Number: 5,413,583
[45] Date of Patent: May 9, 1995

[54] FORCE LIMITING ARRANGEMENT FOR NEEDLE HOLDER FOR ENDOSCOPIC SURGERY

[75] Inventor: Udo Wohlers, Hamburg, Germany

[73] Assignee: Ethicon, Inc., Somerville, N.J.

[21] Appl. No.: 57,236

[22] Filed: May 4, 1993

[30] Foreign Application Priority Data

May 21, 1992 [DE] Germany .................. 42 16 875.9

[51] Int. Cl.6 .............................................. A61B 17/00
[52] U.S. Cl. ..................................... 606/206; 606/148
[58] Field of Search .............................. 606/205-209, 606/139, 142, 148, 174; 128/749, 751

[56] References Cited

U.S. PATENT DOCUMENTS

| 1,659,112 | 2/1928 | LittleJohn | 606/205 |
| 2,455,833 | 12/1948 | Trombetta | 606/139 |
| 4,122,856 | 10/1978 | Mosior et al. | 606/174 |
| 4,898,157 | 2/1990 | Messroghli et al. | 606/147 |
| 5,009,661 | 4/1991 | Michelson | 606/205 |
| 5,197,970 | 3/1993 | Green et al. | 606/139 |
| 5,201,743 | 4/1993 | Haber et al. | 606/205 |
| 5,250,056 | 10/1993 | Hasson | 606/206 |
| 5,263,958 | 11/1993 | deGuillebon et al. | 606/174 |

FOREIGN PATENT DOCUMENTS

| 0342402 | 11/1989 | European Pat. Off. | |
| 0406724 | 1/1991 | European Pat. Off. | 606/139 |
| 3601166 | 7/1987 | Germany | 606/205 |
| 4010775 | 10/1991 | Germany | |
| 4131176 | 4/1993 | Germany | 606/205 |
| 1097311 | 6/1984 | U.S.S.R. | 606/174 |

Primary Examiner—Stephen C. Pellegrino
Assistant Examiner—Nancy Mulcare
Attorney, Agent, or Firm—Paul A. Coletti

[57] ABSTRACT

A needle holder for endoscopic surgery consists of a front forceps with clamping jaws, an instrument tube in which a longitudinally displaceable pull rod is guided, and a rearward grip arrangement which drives an adjustment element connected to the pull rod, and a spring element for the reduction of force from the grip arrangement. A force-limiting coupling is formed according to the invention within the adjustment element.

1 Claim, 2 Drawing Sheets

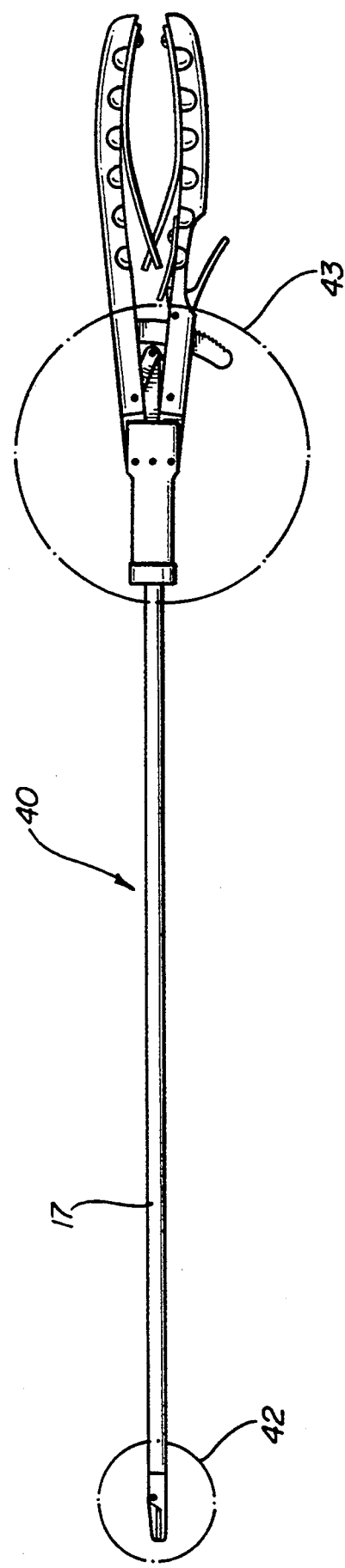
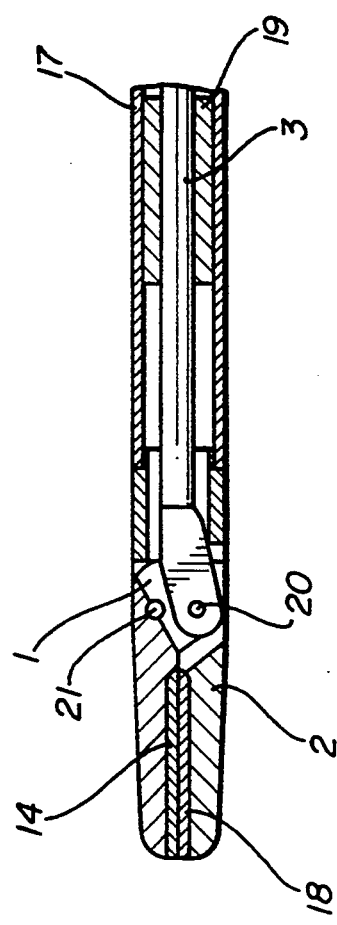
FIG-1
FIG-2

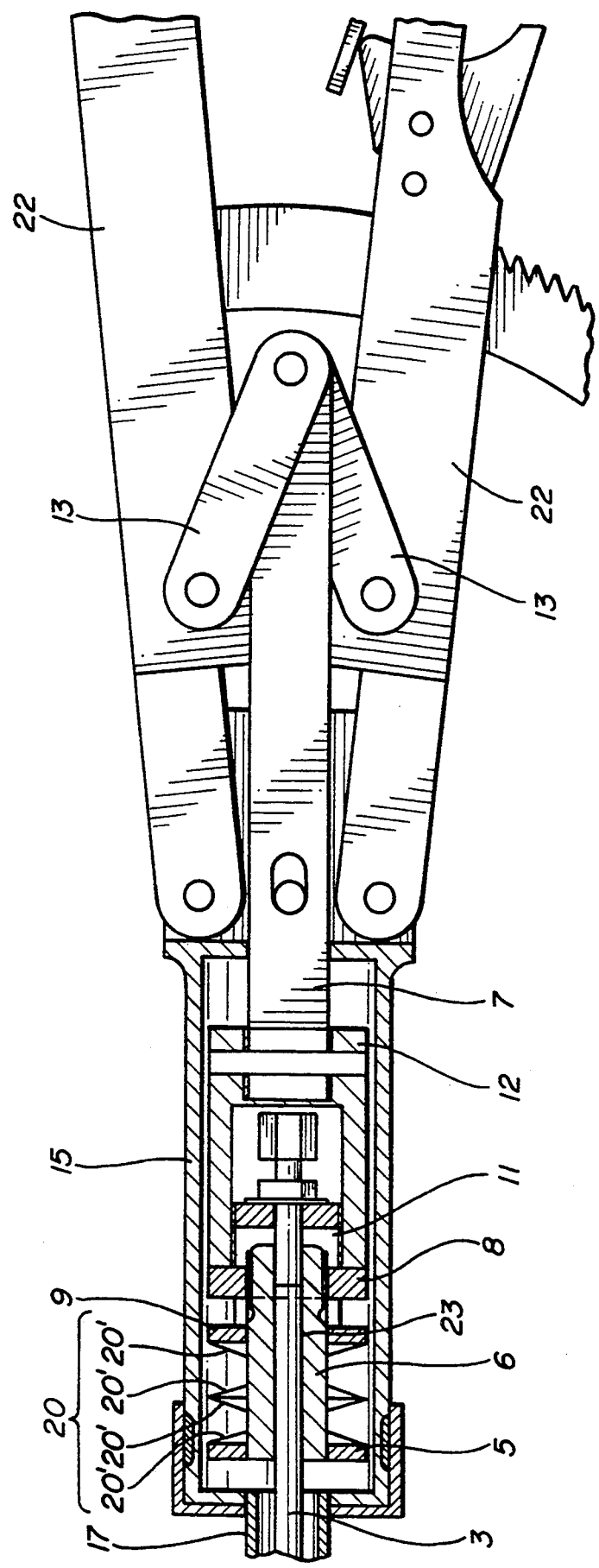

FORCE LIMITING ARRANGEMENT FOR NEEDLE HOLDER FOR ENDOSCOPIC SURGERY

FIELD OF THE INVENTION

The invention relates to a needle holder for laparoscopic operations which consists of a front forceps zone, an instrument tube with a pull rod guided in axially displaceable manner within the tube, a rearward grip arrangement which, when actuated, drives an adjustment element connected to the pull rod, and a spring element for the reduction of force from the grip arrangement onto the pull rod.

BACKGROUND OF THE INVENTION

In modern minimally invasive surgery, the instruments needed for the procedure are introduced into the inside of the body, for example into the abdominal cavity, through cannulae and guided under the control of a likewise introduced endoscope or under X-ray observation and actuated for individual operation steps. Such operations techniques are used for example in laparoscopic cholecystectomy and appendectomy.

Intraabdominal sutures must be provided in these and similar operations. The sutures are created using special surgical needles which are held from outside the body with a needle holder introduced through a cannula and guided by the operator. Such needle holders are provided with two clamping jaws which are movable towards each other to grasp a needle in the manner of forceps between the clamping jaws. One or both of the clamping jaws are opened and closed by a push- or pull-rod guided in the instrument tube of the needle holder.

The position at which the needle lies between the clamping jaws is not predetermined, i.e. the needle can lie well to the rear, near the axis of rotation of the clamping jaw, so that when the jaws grasp the needle, they remain relatively widely opened. Or the needle can lie well forward, near the distal ends of the clamping jaws, so that when the jaws grasp the needle, they are largely closed. Efforts must be made to ensure that the force exerted by the clamping jaws is as independent as possible from the extent to which the grip or the clamping jaws are closed.

Another disadvantage with such holders or forceps is that, because the grip is very large in relation to the clamping jaws, it is very difficult for the user to measure the force exerted on the clamping jaws. The clamping jaws are frequently pressed against each other with too great a contact pressure if the operator closes a gripping member, so that the clamping jaws encounter a resistance lying between them. This can easily result in damage to the clamping jaws, to their bearings or in the transmission of force, and the life of the instrument is reduced overall through overloading. It is known in this regard to provide force-limiting mechanisms in the transmission from the grip onto the clamping jaws.

With the medical forceps described in DE-OS 40 10 775 with a fixed and a swivellable jaw part, a grip arrangement with a fixed and a swivellable grip part is provided. The movement of the swivellable rip part is transmitted via a push- or pull-rod onto the swivellable jaw part. To limit the compressive force at the mouth parts, the swivellable grip part is divided into two parts which are connected to each other by a bending spring element. As the bending spring element is deflected when the jaw parts encounter resistance, the force onto the jaw parts is limited even if the grip is closed to the greatest possible extent.

SUMMARY OF THE INVENTION

The object of the invention is to create a needle holder for endoscopic surgery in which the action of force on the clamping jaws is limited regardless of the closure position of the grip arrangement and which can be carried out regardless of the special shape of the grip arrangement.

According to this invention an adjustment element is provided, which is driven in longitudinal direction upon closure of the grip arrangement. The proximal end of the adjustment element contains a sleeve arrangement, into which the pull rod is inserted so as to be displaceably guided therein. The sleeve arrangement comprises at its distal end a first abutting surface against which a compression spring lies. The compression spring rests with its opposite end on a second abutting surface which is attached to the pull rod in the area inserted into the sleeve arrangement.

As the pull rod is displaceably guided in the sleeve arrangement, a tensile force exerted by the adjustment element on the sleeve arrangement is transmitted from the first abutting surface via the compression spring onto the second abutting surface, and thus onto the pull rod. If, upon closure of the clamping jaws, there is resistance to the further movement of the pull rod, the compression spring controls the force exerted on the adjustment element even if the grip arrangement is closed further. As a result, when the closure of the grip arrangement is complete, the displacement and consequently the force of the adjustment element is not transmitted onto the pull rod. Therefore the force exerted on the clamping jaws holding the needle secured at the pull rod is limited.

For purposes herein, the term "sleeve arrangement" refers to any formations of two coaxially lying rods in which one rod is displaceable in longitudinal direction within the other.

DESCRIPTION OF THE DRAWINGS

The invention is explained below, with reference to an embodiment, in the drawings which show:

FIG. 1 an overall view of the needle holder;

FIG. 2 the front part of the needle holder with the clamping jaws; and

FIG. 3 the arrangement according to the invention for the transmission of force from the grip arrangement onto the pull rod of the needle holder.

DETAILED DESCRIPTION OF THE INVENTION

FIG. 1 shows needle holder 40 with a clamping jaw zone 42 lying at the distal end, the instrument tube 17 connecting thereto, and the transmission mechanism 43 from the rearward grip arrangement onto the pull rod 3 (FIGS. 2 and 3) guided in the instrument tube 17.

In FIG. 2, the clamping jaw zone at the distal end is shown magnified. The needle holder mechanism comprises a fixed clamping jaw 18 and a swivellable clamping jaw 14 to which the pull rod 3 is hingedly connected at pin 20, so that jaw 14 pivots about pin 21. In the instrument tube 17, the pull rod 3 is guided along seal surfaces 19.

In FIG. 3, a magnified view of the arrangement for force transmission is shown in section. Arranged[in the instrument tube 17 is the longitudinally displaceable pull rod 3 which is coupled with the movable clamping jaw 14 at the front forceps zone 1 (shown magnified in FIG. 2). The forceps-like grip arrangement at the rearward end of the instrument is actuated by closure of the handle parts 22 towards each other, whereby a longitudinal movement, to the right in the representation of FIG. 3, is transmitted via the levers 13 onto the adjustment element 7. In FIG. 3, the adjustment element 7 is already in the retracted position. The adjustment element. 7 is firmly connected to a sleeve arrangement which comprises a bushing segment 12, i.e., a cylindrical casing, at which lateral zones are removed on both sides, parallel to the axis of the cylindrical casing. A disk segment 8, formed to correspond to the cross-section of the bushing segment 12, is attached to the bushing segment 12 at its distal end. The disk segment 8, at which lateral zones are removed corresponding to the bush segment 12, is secured to a cylindrical bushing 6. The cylindrical bushing 6 has a central bore 23 which holds push rod 3.

The pull rod 3 is displaceably guided in the bushing 6 of the sleeve arrangement 6, 8, 12. Attached to the pull rod 3 in the zone inside the bushing segment 12 is a bracket 11 which holds the disk segment 8 and carries at its distal end a first abutting surface 9 in the form of a disk which encloses the bushing 6, but is displaceable against it. In a distal direction to the first abutting surface 9 is the second abutting surface 5 which is formed by a disk which is firmly connected to the bushing 6 of the sleeve arrangement 6, 8, 12. Between the first abutting surface 9 (firmly connected to the adjustment element) and the second abutting surface 5 (firmly connected to the pull rod 3) lies a compression spring 20. The compression spring 20 is formed by a sequence of cup springs 20' lying one behind the other. Through this spring 20 a high elasticity constant can be provided within a short portion of the instrument 40. The elasticity constant and therefore the maximum force exerted on the jaw elements can also be pre-set through the number of cup springs.

The proximal end of the pull rod 3 lies, in the unloaded case of the compression spring 20, against an abutment surface of the bushing segment 12 so that, upon opening of the grip arrangement, the pushing movement of the adjustment element 7 is transmitted onto the pull rod 3 and the clamping jaw 14 is opened.

In use, therefore, as the pull rod is displaceably guided in the sleeve arrangement, a tensile force exerted by the adjustment element on the sleeve arrangement is transmitted from the first abutting surface via the compression spring onto the second abutting surface, and thus onto the pull rod. If, upon closure of the clamping jaws, there is resistance to the further movement of the pull rod, the compression spring controls the force exerted on the adjustment element even if the grip arrangement is closed further. As a result, when the closure of the grip arrangement is complete, the displacement and consequently the force of the adjustment element is not transmitted onto the pull rod. Therefore the force exerted on the clamping jaws holding the needle secured at the pull rod is limited.

The invention will be understood for the attached claims and their equivalents.

I claim:

1. An endoscopic instrument containing a pair of jaws connected to a pull rod, said pull rod reciprocal through an elongated tube, said pull rod capable of actuation of said jaws, and a handle connected to said pull rod, said handle containing at least one actuating lever pivotable on said handle for operating said pull rod; and a mechanism comprising an adjustment element placed between said lever and said pull rod such that the force imparted by said lever on said pull rod is controlled by said adjustment element, and wherein said adjustment element comprises a plurality of cup springs lying one behind the other within said handle, and said pull rod reciprocable within said cup springs.

* * * * *